United States Patent [19]

Giantonio et al.

[11] Patent Number: 5,486,465
[45] Date of Patent: Jan. 23, 1996

[54] TEICOPLANIN RECOVERY PROCESS

[75] Inventors: Anacleto Giantonio, Milan; Gianbattista Panzone, Cornaredo, both of Italy

[73] Assignee: Gruppo Lepetit S.p.A., Gerenzano, Italy

[21] Appl. No.: 413,971

[22] Filed: Mar. 29, 1995

Related U.S. Application Data

[63] Continuation of Ser. No. 317,422, Oct. 4, 1994, abandoned, which is a continuation of Ser. No. 196,889, Feb. 15, 1994, abandoned, which is a continuation of Ser. No. 34,007, Mar. 19, 1993, abandoned, which is a continuation of Ser. No. 764,658, Sep. 24, 1991, abandoned.

[30] Foreign Application Priority Data

Oct. 1, 1990 [EP] European Pat. Off. ............ 90118778

[51] Int. Cl.$^6$ .................................................. C07K 14/365
[52] U.S. Cl. .................. 435/70.1; 435/71.1; 435/71.3; 530/317
[58] Field of Search ............. 530/317; 435/71.1, 435/71.3

[56] References Cited

U.S. PATENT DOCUMENTS

| | | | |
|---|---|---|---|
| 4,239,751 | 12/1980 | Coronelli et al. | 424/169 |
| 4,696,817 | 9/1987 | Snipes et al. | 424/118 |
| 4,742,045 | 5/1988 | Verma et al. | 530/317 |
| 4,994,555 | 2/1991 | Panzone et al. | 530/344 |

*Primary Examiner*—Howard E. Schain
*Attorney, Agent, or Firm*—J. Michael Dixon

[57] ABSTRACT

The present invention relates to a method for extracting teicoplanin $A_2$ from a whole culture fermentation broth by filtration of the mycelium in an alkaline medium and recovery by extraction of the filtered fermentation broth with organic solvents or mixtures thereof or by adsorption onto suitable matrixes.

5 Claims, No Drawings

TEICOPLANIN RECOVERY PROCESS

CROSS-REFERENCE TO RELATED APPLICATION

This is a continuation of application Ser. No. 08/317,422, filed Oct, 4, 1994, now abandoned, which is a continuation of application Ser. No. 08/196,889,filed Feb. 15, 1994, now abandoned, which is a continuation of application Ser. No. 08/034,007, filed on Mar. 19, 1993, now abandoned, which is a continuation of application Ser. No. 07/764,658, filed Sep. 24, 1991, now abandoned, herein incorporated by reference.

The present invention relates to a method for extracting teicoplanin $A_2$ from a whole culture fermentation broth by filtration of the mycelium in an alkaline medium and recovery by extraction of the filtered fermentation broth with organic solvents or mixtures thereof or adsorption onto suitable matrixes.

Teicoplanin is an antibiotic produced by cultivating the strain *Actinoplanes teichomyceticus* ATCC nov. sp. 31121 in a culture medium containing assimilable sources of carbon, nitrogen and inorganic salts.

The main product resulting from the above mentioned strain is a mixture of three main factors ($A_1$, $A_2$ and $A_3$) originally referred to as teichomycin (U.S. Pat. No. 4,239, 751).

The more recent teicoplanin preparations obtained by purification of the product recovered from the fermentation broth and suitable for chemotherapeutic use in the treatment of infections caused by gram-positive organisms (A. H. Williams et al.: Journal of Hospital Infection (1986); 7, Suppl. A, 101–103 and D. Greenwood: Journal of Antimicrobial Chemotherapy (1988); 21, Suppl. A, 1–13) contain a complex of five structurally similar substances which had been originally referred to, as whole, as teichomycin factor $A_2$. The above mentioned five closely related components have been successively isolated and characterized as single components of the complex which was then currently designated and referred to in the scientific papers and patent literature as "teicoplanin $A_2$" or "teicoplanin complex".

The ratios of the mentioned five related substances in the teicoplanin complex can vary according to the fermentation conditions and the precursors added to the fermentation medium as described in the European Patent Application Publication No. 204179.

The process of the present invention can be advantageously applied to any industrial scale fermentation process used to prepare teicoplanin complex or any of its components.

The fermentation broth or the process stream from which the aqueous solution containing the antibiotic activity is obtained, are produced according to the standard pilot or industrial scale procedures and can include also those cases where different additions of appropriate precursors are made during the fermentation process in order to selectively increase the ratio of the single major components of a glycopeptidic antibiotic complex. See for instance the already cited European Patent Application Publication No. 204179.

U.S. Pat. No. 4,239,751 teaches a method of recovering teicoplanin complex from the fermentation broth and isolating the antibiotic factors.

In the method described in U.S. Pat. No. 4,239,751, the fermentation broth is filtered at pB 3.5 in order to remove the mycelial mass leaving a mycelial cell cake. The filtered fermentation broth is then mixed with a water immiscible organic solvent, such as, halogenated $C_1$–$C_4$ hydrocarbons or $C_4$–$C_6$ alkanols, in which the antibiotic mixture is soluble. The water immiscible organic solvent is then separated from the filtered fermentation broth by high-speed centrifugation, concentrated to about ⅒ to 1/20 of its original volume, cooled and allowed to stand until a precipitate (the antibiotic) forms which is recovered by filtration.

However, it is known that part of the teicoplanin produced by the fermentation of *Actinoplanes teichomyceticus* ATCC 31121 is bound to the mycelium. Therefore, according to the above mentioned U.S. Patent, it is necessary to carry out a further extraction step of the mycelial cake with aqueous acetone in order to recover additional product. After distillation of the acetone, the aqueous phase is submitted to the same treatment described above for the filtered fermentation broth.

Thus, in conclusion, the method described in U.S. Pat. No. 4,239,751 requires the obtainment of two crops to isolate the product i.e., one crop recovered from the filtered broth extraction with butanol and another crop coming from the semi-exhausted mycelium (extraction with acetone/water followed by evaporation and extraction).

In U.S. Pat. No. 4,696,817, in order to avoid the two step process of U.S. Pat. No. 4,239,751 outlined above, an alternative unitary process was proposed.

In particular, said unitary process concerned a method for extracting teicoplanin $A_2$ from the whole culture fermentation broth, essentially by mixing said broth containing the mycelial mass with an effective amount of water miscible solvent, separating the broth/solvent liquid containing the antibiotic activity from the mycelial mass and precipitating the teicoplanin product from the broth/solvent solution.

Unfortunately, the process of U.S. Pat. No. 4,696,817 has the serious drawback (in particular, when the extraction is carried out using the fermentation procedure scaled-up to the industrial level) of necessarily employing large volumes of dangerous toxic water miscible solvents (such as acetonitrile) which makes the teicoplanin extraction potentially unsafe, causing stockage problems of solvents and increased costs due to the necessary recovery and separation of the exhausted mixture of solvents.

Surprisingly, we have found that with the process of the invention, it is possible to recover teicoplanin $A_2$ in higher yields with respect to the most pertinent art cited above, without carrying out two parallel processes (i.e. one on the filtered broth and the other on the mycelial cake) and at the same time avoiding the undesirable use of large volumes of water miscible solvents.

In fact, it has been found that separation of the myceliumat a pH value at least higher than 10 solubilizes at least 90% of the total activity of the antibiotic.

Thus, the overall yields of the process to make pure teicoplanin could result increased by at least 50% working only on the filtered broth.

Of course, a second extraction of the mycelium at the same pH value of the first extraction would allow to extract more than 95% of the total antibiotic activity.

It is therefore an object of the present invention a process for extracting teicoplanin $A_2$ from a whole culture fermentation broth which comprises:

a) separating the mycelium by filtration from the broth maintaining constant the pB during said filtration at a value at least higher than 10 and at a temperature which essentially avoids epimerization of teicoplanin, and b) separating teicoplanin $A_2$ from the filtered broth.

The main problem to overcome when operating with the process of the present invention, is the epimerization of the teicoplanin molecules which usually occurs in alkaline medium and produces practically inactive materials.

In fact, it is well known that teicoplanin or its acidic hydrolysis products in basic medium (pH>10) give rise to epimeric species which retain little antibiotic activity. About the structure of epimers and the basic hydrolysis studies carried out on teicoplanin, see for instance J. C. J. Barna et al. in "The Journal of Antibiotics", Vol. XXXVII; No. 10, pp 1204–1208.

Unexpectedly, we found that the evaluation of the stability of teicoplanin aqueous solutions carried out at a pH value of 11, showed that epimerization depends on the temperature of the solution and is practically negligible from the freezing point of the solution to room temperature, also allowing to stand the solution at pH 11 for many hours.

In particular, the increase of epimers on the total amount of antibiotic was found extremely low maintaining the teicoplanin solution at pH 11 at a temperature of 5° C. for 72 hours and at room temperature for 24 hours while by increasing the temperature to 40° C. the percentage of epi-substances was about 30% calculated by HPLC after 15 hours.

Therefore, references in this specification, including the claim, to "a temperature which essentially avoids epimerization of teicoplanin" mean a temperature which is comprised between the freezing point of the solution (not included) and room temperature, and preferably a temperature comprised between 5° C. and 10° C.

An effective method for checking the level of epi-substances present in the filtered broth is to follow the filtration by HPLC.

In order to have a suitable filtered broth the epi-substances should be less than 5% calculated by HPLC.

All the HPLC controls were carried out by using a Hewlett Packard apparatus Model 1084 equipped with a UV (254 mµ) detector and a reserve phase C18 prepacked column (Erbasil 5, 250×4 mm).

The mobile phases were: (A) 0,02M aqueous $NaB_2PO_4$/$CH_3CN$ 95:5 (v/v), (B) 0.02M aqueous $NaH_2PO_4$/$CB_3CN$ 25:75 (v/v). The gradient elution was from 8% of B to 55% of B in 40 minutes. Flow rate 1.5 ml/min.

The filtration of the mycelium can be carried out according to the well known methods used in the art.

In particular, the filtration may be carried out on rotary vacuum drums covered by a filter aid, such as for example a diatomaceous earth inert material (Clarcel FLO/MA or Byflo panels).

The pH value at which the filtration occurs is particularly critic according to the process of the invention. It has been noticed that the concentration of antibiotic activity in the fermentation broth increases by enhancing the pH values.

It was found that, in order to have higher yields, the pH value has to be not lower than 10 and preferably comprised between 10.5 and 11.5, more preferably 11. At the pH value of 12 the epimerization could increase too much.

Furthermore, it was noticed with various teicoplanin broths that the pH tends to decrease with time, independently from the starting value. Since filtration at a pH lower than 10 reduces the amount of activity extracted from the mycelium, the pH should be kept constant during the filtration by adding a suitable diluted alkaline solution.

The suitable diluted alkaline solution may be choosen for example among diluted caustic solutions such as aqueous NaOB or aqueous KOH solutions. The type and concentration of the caustic solution is not a critic parameter of the invention. The concentration may be for instance comprised between 5% and 15%. Since teicoplanin is very sensitive to high alkaline pH, the addition of said diluted alkaline solutions should be preferably carried out under good agitation conditions to avoid locally high concentrations.

Trials were made to determine how long it takes for the broth to reach the equilibrium concentration at pH 11 before carrying out the filtration. It was seen that few minutes are practically enough.

The separation of teicoplanin from the filtered broth can be carried out according to any method known in the art.

A method particularly suitable, is described in European Patent Application Publication No. 241758. It comprises contacting the filtered solution with a polyamide column chromatography resin capable of absorbing the teicoplanin activity, separating the resin from the aqueous solution and making the elution with a solvent mixture of water and one or more mixable organic solvents selected from lower alkanol, acetone, methyl ethyl ketone, tetrahydrofuran, dioxane and the like.

The adsorption of teicoplanin from the filtered broth is preferably carried out at a pH value comprised between 5 and 8 so that it is necessary to acidify the solution coming from the filtration.

Any mineral or organic acid can be used to reach the suitable pH value of the adsorption by polyamide resin.

The suitable polyamide resin according to the European Patent Application Publication No. 241758 can be selected from polycaprolactame, nylon 6/6, nylon 6/9, nylon 6/10, nylon 6/12 and cross linked polyvinylpyrrolidone.

The following examples will make more understandable the invention without having any limiting purpose.

EXAMPLE 1

Samples coming from the pilot plant of different whole culture fermentation broths of *Actinoplanes teichomyceticus* ATCC 31121 were brought under stirring to pH 11 with 10% NaOH and filtered through a cake of Clarcel Flo/Ma filter aid at 5° C.

For comparison, other samples from the same whole cultured fermentation broths were filtered at pH 6.7–8 according to the procedure outlined above.

The antibiotic concentrations in the filtered broths were evaluated by HPLC. For the HPLC conditions see the specification above.

The results are summarized in Table I below.

TABLE I

| Batch No. | % Increase obtained at pH 11 vs. pH 6.7–8 |
| --- | --- |
| 1 | 66.2 |
| 2 | 90.6 |
| 3 | 74.5 |
| 4 | 68.5 |
| 5 | 67.6 |

EXAMPLE 2

700 Ml of teicoplanin $A_2$ fermentation broth were brought under stirring to pH 11 with 10% aqueous NaOH and filtered after 10 minutes substantially following the same procedure of Example 1.

After the filtration 600 ml of filtered broth were recovered with a yield of 85.7% of the starting antibiotic activity.

EXAMPLE 3

(Comparative Experiment)

Prior-art method (U.S. Pat. No. 4,239,751 column 5 lines 1–48)

a) By starting from the same amount of the same fermentation broth used in the previous example, a filtration by conventional procedures (pH 8) was carried out. The filtered medium was adjusted at pB 3.5 by addition of HC18% and then extracted twice with butanol (180 ml). The two organic extracts were combined and the concentration of extracted teicoplanin $A_2$ was measured by HPLC. The yield of antibiotic activity of this step was about 26.1%.

b) The mycelial cake obtained by the filtration described above was washed with water at pH 3.5, dried under vacuum and then extracted twice with a mixture water-acetone 60/40 to yield a total of 800 ml of filtered solution corresponding to a 38.7% total yield of antibiotic activity.

Therefore, by employing the elaborate method described above (a+b), a total Mount of 64.8% of teicoplanin $A_2$ are extracted from the original broth into the two solutions to be worked out for final recovery.

EXAMPLE 4

(Comparative Experiment)

Prior-art method (U.S. Pat. No. 4,696,817)

The same amount of the same broth used in the previous examples were mixed with different volumes of solvents (see Table II below) to give from 20 to 60 percent by total volume mixture of the solvent in the broth. After 5 minutes mixing period with continuous agitation, the samples were centrifuged, the exhausted mycelium discharged, and the supernatant (which can be further worked out for final recovery) was assayed for teicoplanin $A_2$ content according to a standard HPLC method.

The results are summarized in Table II below:

TABLE II

| % Solvent (by volume) | Total volume after filtration of the mycelium (ml) | Total yield of teicoplanin $A_2$ extracted into the solution (%) |
| --- | --- | --- |
| 30% Acetonitrile | 900 | 84.4 |
| 20% Acetonitrile | 775 | 74.0 |
| 30% Acetone | 1300 | 84.9 |
| 40% Acetone | 1067 | 80.0 |
| 30% Acetone | 900 | 73.0 |
| 20% Acetone | 775 | 64.5 |
| 40% n-Propanol | 1067 | 88.7 |
| 25% MBK | 834 | 76.6 |

As can be noted from the comparison of the data reported in Table II above and the data of Example 2, the total yield of antibiotic activity of the method of the present invention is comparable with (and in many cases higher than) the yield of the process described in U.S. Pat. No. 4,696,817 notwithstanding with the present method undesirable mixtures of solvents are not used.

EXAMPLE 5

700 Ml of teicoplanin $A_2$ fermentation broth were brought under stirring at pH 11 with 10% aqueous NaOH and filtered after 10 minutes. The filtered solution was then brought back to pH 8 with 10% aqueous HCl and then passed through a 2.5×50 cm glass column filled with 250 ml of polyamide resin (Polyamide-CC 6 for column chromatography, particle size 50–160 µ, apparent density 0.20 g/ml, Macbetsy Nagel, W. Germany) and kept under vacuum with suction from the bottom. The average flow rate was 100 ml/cm$^2$ h. The exhausted broth (700 ml) contained about 7% of the starting teicoplanin activity and more than 80% of all the more polar components of the broth (unwanted solids and colored organic materials). After washing with 2 bed volumes of deionized water, the resin slution was carried out with 5 l of a mixture of 9/1 methanol/water (v/v) containing a gradient from 0.3 to 1.0 g/l of sodium carbonate.

The eluates were collected in seven fractions of 700 ml each. Each fraction was neutralized to pH 7 with aqueous mineral acid and then analyzed by HPLC analysis. Only five fractions (3,5 liters) of the eluate were combined and the resulting solution (containing more than 90% of the eluted activity) was concentrated-under reduced pressure at 40°–50° C. to 0.6 liters of aqueous residual suspension.

10.0 Liters of acetone were added to the above concentrated teicoplanin suspension under stirring.

The precipitate was left to stand for 3 hours at room temperature and the clear surnatant acetone was decanted.

The solid was separated by filtration and the cake washed with acetone at room temperature.

The product was dried overnight under vacuum at room temperature.

Teicoplanin 85% pure by HPLC was obtained with a recovery yield of 74.3% on the starting microbiological activity contained in the fermented broth (water and solvent content= 10.6%, by weight; inorganic residue: 2.8%, by weight).

The 12 l mother liquors contained about 10% of the starting teicoplanin.

We claim:

1. A process for recovering teicoplanin $A_2$ from a whole culture fermentation broth, containing a mycelial mass produced by the fermentation of *Actinoplanes teichomyceticus* ATCC 31121, which comprises:

a) separating the fermentation broth from the mycelial mass by filtration;

b) raising the pH of the whole culture fermentation broth to a level greater than 10, but less than 12, prior to initiating said filtration and maintaining this pH range while said filtration is carried out;

c) maintaining the temperature of the whole culture fermentation broth at a temperature no greater than room temperature while said filtration is carried out and;

d) recovering said teicoplanin $A_2$ from the filtered fermentation broth.

2. A process according to claim 1 wherein the filtration is carried out at a pH value between 10.5 and 11.5.

3. A process according to claim 1 wherein the filtration is carried out at a pH value of about 11.

4. A process according to claim 2 wherein the temperature at which the filtration is carried out is between 5° C. and 10° C.

5. A process according to claim 4 wherein the recovery of teicoplanin $A_2$ from the filtered broth is carried out by contacting said filtered broth with a polyamide column chromatography resin capable of adsorbing the teicoplanin activity for an appropriate period of time to adsorb said activity, separating the resin from the filtered broth and eluding said polyamide column with a solvent mixture of water and one or more mixable organicssolvents to recover the Teicoplanin $A_2$ from said polyamide column.

\* \* \* \* \*